United States Patent [19]
De Rowe

[11] Patent Number: 6,042,380
[45] Date of Patent: Mar. 28, 2000

[54] INFLATABLE DENTAL IMPLANT FOR RECEIPT AND SUPPORT OF A DENTAL PROSTHESIS

[75] Inventor: Ari De Rowe, Moshau Salit, Israel

[73] Assignee: Discotech Medical Technologies, Ltd., Herzelia, Israel

[21] Appl. No.: 09/199,678

[22] Filed: Nov. 25, 1998

Related U.S. Application Data

[60] Provisional application No. 60/066,778, Nov. 25, 1997.

[51] Int. Cl.[7] ........................................................ A61C 8/00
[52] U.S. Cl. ........................... 433/173; 433/173; 433/175; 433/177; 433/172
[58] Field of Search .................................. 433/173, 175, 433/177, 172

[56] References Cited

U.S. PATENT DOCUMENTS

| | | | |
|---|---|---|---|
| 3,343,263 | 9/1967 | Henlotter | 433/175 |
| 4,686,973 | 8/1987 | Frisch | 606/95 |
| 4,888,024 | 12/1989 | Powlan | 623/23 |
| 4,906,190 | 3/1990 | Michna | 433/175 |
| 5,037,445 | 8/1991 | Sander et al. | 623/66 |

*Primary Examiner*—John J. Wilson
*Attorney, Agent, or Firm*—Levisohn, Lerner, Berger & Langsam

[57] ABSTRACT

An expandable dental implant which is less traumatically inserted and can immediately receive functional loading to support a dental prosthesis upon insertion into the patient's mouth. The expandable implant is constructed as an inflatable balloon, which has a first, relatively smaller diameter prior to insertion into the patient's mouth. The implant is provided with an insertion end, for insertion into a formed bore in the patient's jaw bone. Upon insertion into the bone, the balloon can be inflated into a second, larger diameter profile by filling the hollow interior of the balloon using an appropriate hardening material, which applies pressure against the interior walls of the implant, allowing the implant to inflate within the bone and to fixate. Upon inflation of the implant, a dental crown can immediately be added to the implant's attachment end.

16 Claims, 4 Drawing Sheets

INFLATABLE DENTAL IMPLANT FOR RECEIPT AND SUPPORT OF A DENTAL PROSTHESIS

RELATED APPLICATIONS

The present application claims all rights of priority to U.S. Provisional Patent Application Ser. No. 60/066,778, filed Nov. 25, 1997, and entitled "Implantable Dental Implant for Receipt and Support of a Dental Prosthesis," the disclosure of which is fully incorporated herein by reference.

FIELD OF THE INVENTION

The present invention relates to an inflatable bone implant for receiving and supporting a dental prosthesis.

BACKGROUND OF THE INVENTION

The present invention relates generally to the technical field of dentistry and more particularly to an inflatable dental implant installed into a patient's jaw to support a dental prosthesis. Currently, the dental restoration of a patient who has experienced tooth loss is generally accomplished in a two stage process. In the first stage, an artificial dental implant is implanted into the patient's jawbone for future receipt of a dental prosthesis. This implantation is achieved by cutting the gingiva, exposing the bone, drilling a hole within the bone, and inserting the implant. The artificial implant is left in the jawbone for an extended period of time, while the implant integrates into the bone to form a stable attachment surface. Upon stable integration, a second stage is begun which involves the attachment of a prosthesis to the stable artificial implant. The stage begins with oral surgery to reaccess the implant through the gum, followed by the fabrication of restorative dentition, to build and maintain a prosthesis or artificial tooth which is permanently attached to the implant and within the mouth.

In the present state of the art, most dental implants can not immediately accept functional loading, i.e. the forces exerted upon a dental implant when the patient is chewing food. As a result, when using such implants, as much time as six months may elapse between the installation of the implant into a patient's jaw and the subsequent installation of the prosthesis. During this extended interval of time between implant installation and prosthesis installation, bone will regrow around and into an initially loose implant until that implant becomes firmly fixed within the jaw. Once the implant is firmly fixed, the prosthesis can be installed. Installation of the prosthesis after this long period of time requires a second surgery to expose the head of the implant and thereby allow the prosthesis to be attached.

Accordingly, there is a significant need within the art for a dental implant which will immediately accept functional loading. In addition, it is also highly advantageous, and a need within the art, to provide a dental implant which will allow minimal gingival trauma during implant insertion, without the need for large diameter bone drilling to accept the implant diameter.

SUMMARY OF THE INVENTION

It is an object of the present invention to provide a dental implant which, with the dental prosthesis, can be installed in a minimal amount of time with minimal trauma and/or immediately accept functional loading.

It is a further object of the invention to provide a dental implant which can expand, after insertion within the bone, to receive and support a dental prosthesis.

It is a further object of the invention to provide an expandable dental implant which can be inflated upon insertion into the patient's jaw bone and provide a secure fit in the jaw.

It is a further object of the invention to provide a dental implant which can rapidly fixate into the bone.

It is a further object of the invention to provide a dental implant which can immediately accept a dental prosthetic, for example, a crown.

It is a further object of the invention to provide a dental implant which allows minimal gingival trauma during implant insertion.

It is a further object of the invention to provide a dental implant which facilitates soft tissue healing and adaptation.

It is a further object of the invention to provide a dental implant which can be implanted without establishing a void within the jaw upon installation.

It is a further object of the invention to provide a dental implant which permits normal tissue contour around the dental implant and prosthesis.

It is a further object of the invention to provide a dental implant which allows easy, selective removal.

Further objects of the invention will become apparent in conjunction with the disclosure provided herewith.

In accordance with the present invention, a dental implant is provided which can immediately receive and support a dental prosthesis. The expandable dental implant is provided in the form of an inflatable balloon, which has a first, relatively smaller diameter prior to insertion into the patient's mouth, and a hollow interior. The implant is provided with an insertion end, for insertion into a bore drilled in the patient's jaw bone. Upon insertion into the bone, the balloon is then inflated into a second, larger diameter profile. Once the implant has been inserted into the bore of the implant, inflation of the implant is accomplished by filling the hollow interior of the balloon, using an appropriate hardening material, which applies pressure against the interior walls of the implant, allowing the implant to inflate and expand within the bone and to further fixate. Upon inflation of the implant, a screw and dental prosthetic, a crown, can immediately be added to the implant's attachment end. Alternatively, a several week waiting period is provided to allow bone growth around the implant.

In further embodiments of the invention, the implant can be prefabricated with a metal post which extends to the insertion hole and which is designed to receive a prosthesis immediately post-operatively.

In addition, in any of the embodiments of the present invention, the outside surface of the implant, which upon inflation, is placed in contact with the bore of the bone, can be provided with indentations so as to allow and facilitate bone growth into and around the implant to improve implant fixation.

Detailed Description of the Invention and the Preferred Embodiments

In accordance with the present invention, an improved dental implant is provided which can immediately receive functional loading, and which is atraumatically inserted. The dental implant is expandable, allowing insertion in a small profile, with expansion occurring after implantation to achieve the desired full implant diameter. This design further allows implantation of a dental implant with minimal gingival trauma and minimal bone drilling, if at all, during insertion of both the implant and the subsequent prosthesis.

Figure 1:
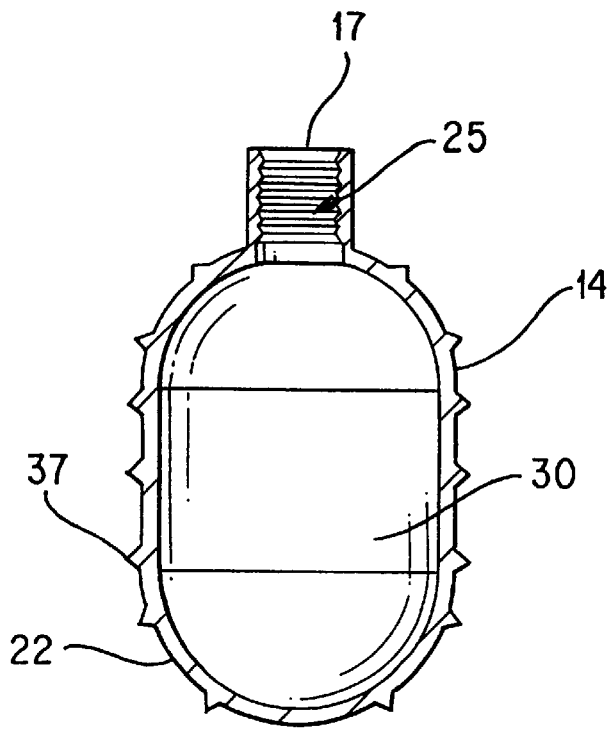
FIG. 1 is a cross sectional view of an inflatable balloon implant including a plunger with external screw threads, in accordance with the present invention, while the implant is in its non-inflated, small profile state.
Figure 2:
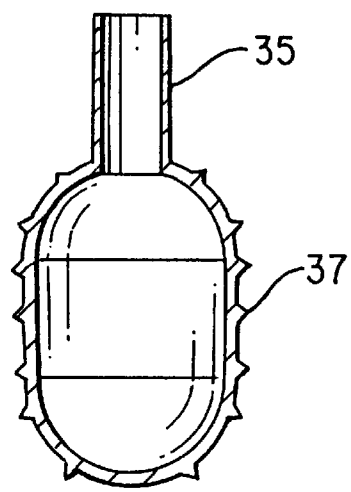
FIG. 2 is a cross sectional view of an inflatable balloon implant including a valve, in accordance with the present invention, while the implant is in its non-inflated, small profile state.

Accordingly, the present invention addresses the shortcomings of the prior art by providing a dental implant 14 in the form of an inflatable balloon, as shown in FIG. 1. Before insertion of the implant, a small diameter bore is drilled or formed within a patient's gingival tissue, and into the patient's jaw bone. This small bore is of a diameter sufficient to receive the implant in its small, non-inflated profile.

The balloon implant 14 includes a tubular barrel having a proximal attachment end 17 to which a dental prosthesis, preferably a single tooth crown or multiple-tooth bridge, may be attached. Implant 14 further includes a distal insertion end 22. Distal insertion end 22 is inserted into the bore formed within the bone of the patient's jaw.

Balloon implant 14 is formed of a thin metal material, preferably of 10 to 300 microns in wall thickness, although larger or smaller walls may be possible as well. The wall thickness is sufficient to maintain structural integrity even upon selective inflation and deflation and, yet, thin enough to allow for ease of inflation, as and when desired. One preferred material is annealed stainless steel 316. Other materials which can be used are biocompatable metals, including, but not limited to, titanium, tantalum, or platinum. Alternatively, the balloon implant can be constructed of a polymer, such as polypropylene, or other suitable materials. A preferred material is titanium, as bone growth into the rough surface of titanium is an advantageous property. In an alternate embodiment, shape memory metal, e.g., Nitinol, may be used which will revert to its austenitic state upon application of heat (e.g., body heat or an external source of heat) or the removal of an applied stress (applicable to stress-induced martensite).

Figure 3:
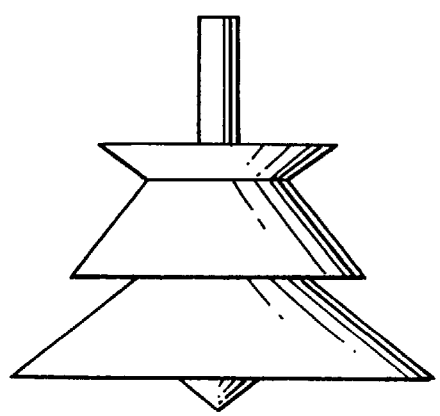
FIG. 3 is a cross sectional view of the inflatable balloon implant of FIG. 1 or 2, after expansion of the implant into its inflated diameter.
Figure 6:
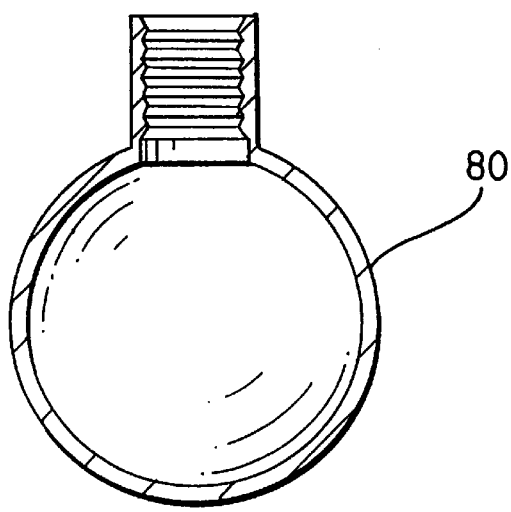
FIG. 6 is a cross sectional view of a further embodiment of the inflatable balloon implant after expansion.
Figure 7:
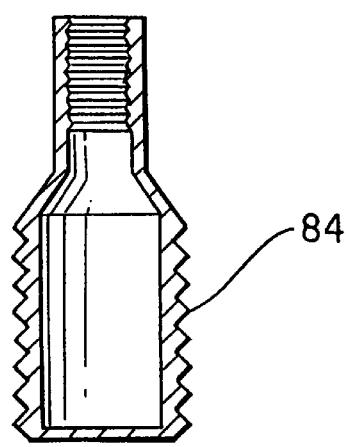
FIG. 7 is a cross sectional view of yet a further embodiment of the inflatable balloon implant after expansion.

Balloon implant 14 includes an opening or valve 25 leading to a cavity 30 within the implant's interior. After insertion into the bore of the jawbone, in the reduced size, a hardening material such as a solidifying cement may be inserted into cavity 30, through opening or valve 25, to serve as a filler material within implant 14. Suitable hardening materials include the cement material MIRACLE MIX, manufactured by GC Corporation, or a solidifying glue such as bone cement. Insertion of the filler material into implant 14 fills the implant cavity 30, causing pressure against the interior walls of the cavity. As the cavity fills, the pressure against the cavity walls causes the implant to radially expand into a larger diameter profile, as shown in FIG. 3. Expansion of the implant, which occurs while the implant is within the bore in the bone, results in an improved, solid and stable fixation of the implant in the bone, immediately from the time of implantation. Upon expansion and/or unfolding, the implant will assume the predetermined shape (as shown in FIGS. 3,6 and 7) or in an alternate embodiment, the implant can expand and conform to the shape of the bore itself, i.e., the balloon actually expands to the shape and size of the cavity. This implant is sufficiently stable to allow for the immediate placement and attachment of a fully functional dental prosthesis to the implant. An inflatable/expandable implant more closely and precisely corresponds to the interior surface/profile of the bore in the bone. Thus, selective undercutting or grooving can be first performed and, then, when inflation occurs, the implant is firmly gripped by the side walls of the bone.

Alternatively, in place of a solidifying cement, an incompressible liquid can be inserted into cavity 30 as the filler material. When a liquid filler material is used, a two way valve 25 may be utilized, as well. In this embodiment, liquid can both pass into the valve, to inflate the dental implant, and selectively be leaked out of the valve, to be used to deflate implant 14 and facilitate implant removal from the bone. In this embodiment, the dental implant is easily removed from the patient's bone, should removal become necessary.

Upon expansion of dental implant 14, a screw and dental crown can be instantly added to build a false tooth or prosthesis upon the attachment end 17 of implant 14. The same screw threads which can be used for accepting the inflating mechanism, can be used for accepting and retaining the screw and crown of the prosthesis. Alternatively, the dental surgeon may wait several weeks until bone growth around the implant is established, if desired. In any of the embodiments of the present invention, indentations or ridges 37 may be provided on the outside surface of dental implant 14, to allow improved bone ingrowth into the dental implant surface.

In an alternative embodiment of the invention, dental implant 14 can be provided with a prefabricated metal post 35 which is already attached to the implant 14, and which extends above the gingiva upon implantation of the implant 14 into the bone. This metal post 35 is designed to extend through the insertion hole of the gingiva, and can immediately receive a prosthesis, post-operatively.

Due to the rapid and stable fixation of the balloon implant within the bone, the embodiments of the present invention allow acceptance of functional loading immediately after implantation of the implant within the bone and likewise permits immediate attachment of a prosthesis. The small profile insertion also facilitates soft tissue healing and adaptation immediately upon installation to allow normal tissue growth around the dental prosthesis. The present invention also allows construction of a dental implant which upon installation may be more easily removed should removal become necessary.

Figure 4:
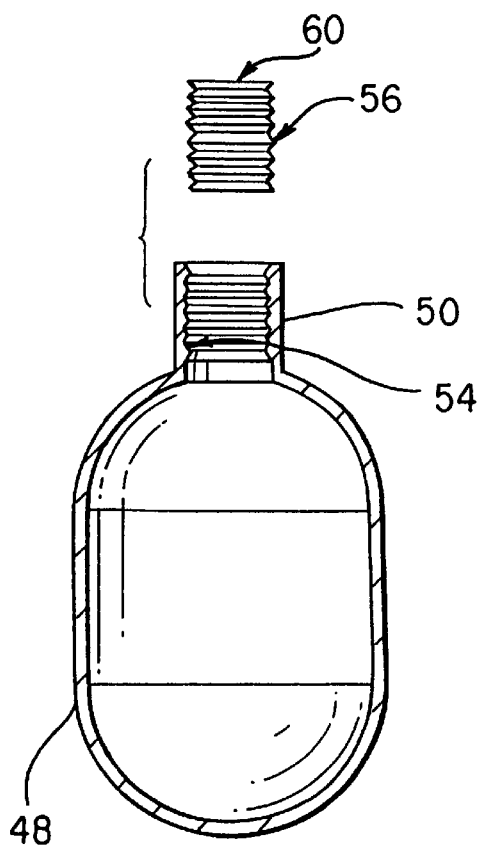
FIG. 4 is a cross sectional view of a further embodiment of the inflatable balloon implant.

Additional embodiments of the invention are shown in FIGS. 4–7. As shown in FIG. 4, in an alternate embodiment of the present invention, an implant 48 is inserted into the bore of the jawbone, again, in its collapsed or reduced in diameter size. The walls of the implant are initially collapsed. This implant, too, is either pre-filled with hardening material or the hardening material may be added through the neck of the implant after installation into the bore of the jawbone.

As shown in FIG. 4, in this embodiment, the neck 50 of the implant 48 is further provided with internal screw threads 54, and a screw or plunger 56. Screw or plunger 56 is provided with external screw threads passing through and mating with the threads of neck 50. The screw 56 is preferably provided, as well, with a rotatable cap 60, at the proximal end of the plunger 56. In use, rotating cap 60 causes the plunger 56 to be pushed into the implant 48. This insertion of the plunger 56 provides radial expansive pressure on the implant's walls, either directly or through compressing the fluid within the implant. The relative movement of the plunger allows precise expansion of the side walls of the implant, to the degree desired, securing the same into the bore within the patient's bone. The cap 60 of the plunger 56 can further serve as an attachment site for securing the prosthesis.

Figure 5:
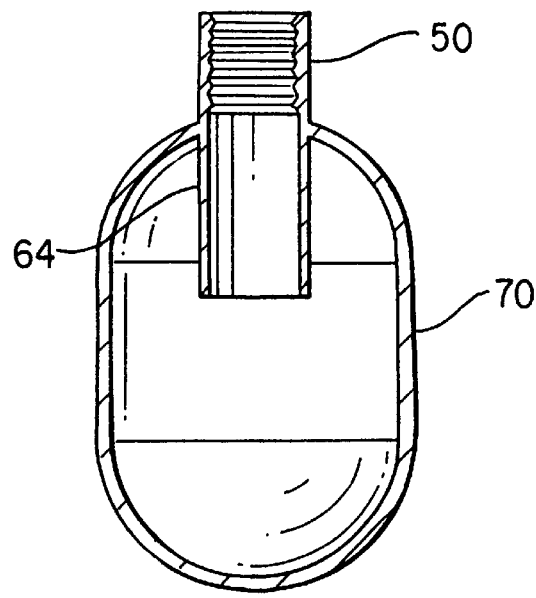
FIG. 5 is a cross sectional view of a further embodiment of the inflatable balloon implant, in which the balloon implant uses a screw or an external source.

Further embodiments of the invention are shown in FIGS. 5 through 7. As shown in FIG. 5, neck 50 of the implant 70 can further be provided with projecting walls 64, which extend or project from neck 50 down into the interior of the balloon implant 70. As shown in FIG. 6, in an alternative embodiment of the invention, body 80 of balloon implant 70, rather than being approximately tubular after expansion, can be approximately spherical or semi-spherical in construction. As shown in FIG. 7, in an alternative or additional embodiment, the external walls of body 84 of balloon implant 70 can be provided with a ridged or undulated surface to promote bone ingrowth into the implant.

As a further alternative design for inflation of the implant, a filler material can be used which changes phase from fluid to solid upon application of an appropriate stimulus from an external source preferably located outside the implant. For example, a fluid can be used which can be made to change phase from fluid to solid (or vice versa), or which changes shape, based upon the application of the stimulus. The outside source can be a source which generates or produces heat, electricity, magnetic fields, ultrasound, radiation, or so forth. Internal body heat can also cause the implant to revert to a predetermined shape, if the implant is made of shape memory material, e.g., Nitinol. Upon application of the stimulus to the fluid, the fluid can be caused to change shape to exert pressure against the walls of the implant to expand, or vice versa to contract.

Figure 8:
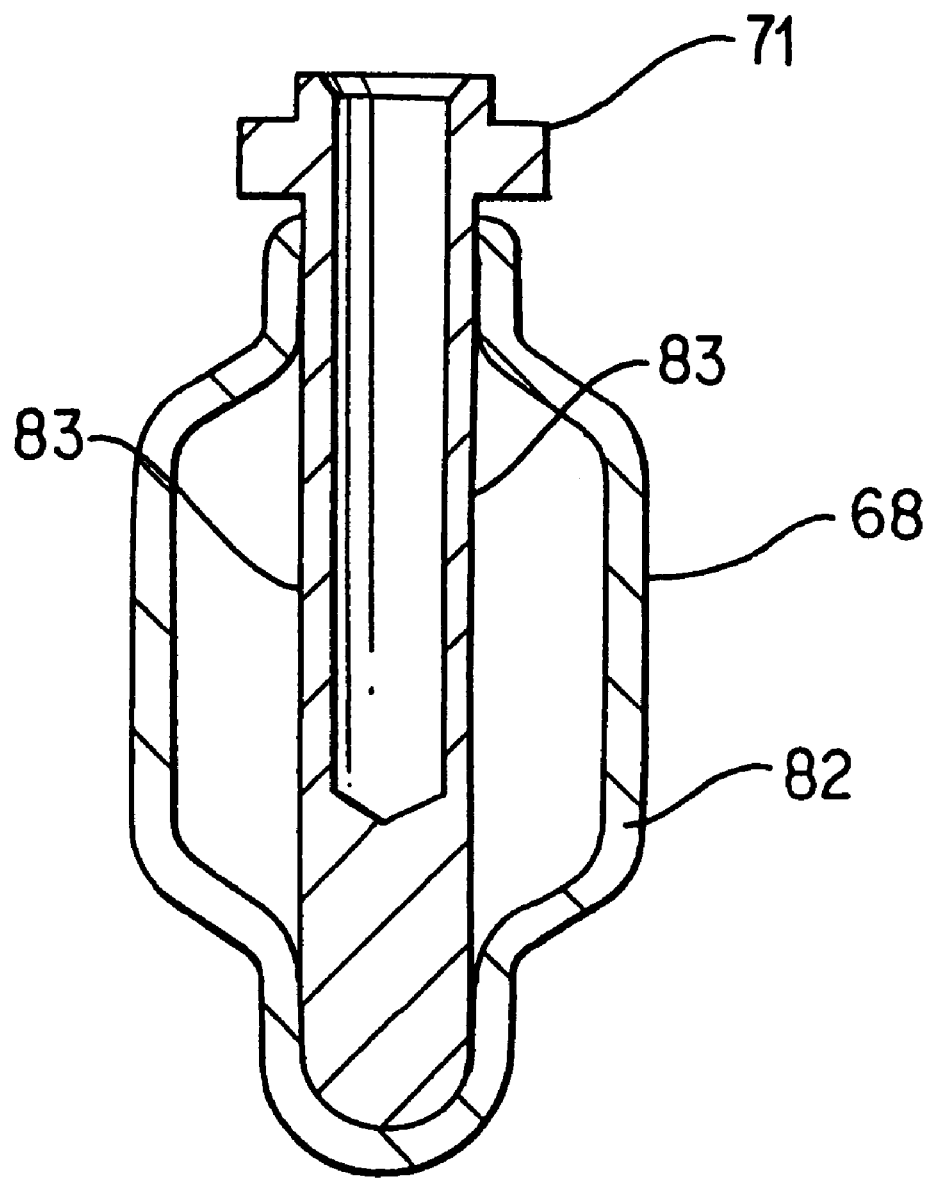
FIG. 8 is a cross sectional view of a further embodiment of the inflatable balloon of the present invention.

Yet a further embodiment of the invention is shown in FIG. 8. As shown therein, a balloon dental implant 68 is provided having a pin 71 surrounded by an inflatable balloon 82. Pin 71 and inflatable balloon 82 can be secured together by any method which will produce a suitably secure attachment. In the preferred embodiment, inflatable balloon 82 and pin 71 are welded together.

Prior to insertion of balloon implant 68, inflatable balloon 82 is compressed from its maximum diameter to a deflated diameter (e.g. by folding or flattening), the deflated diameter being slightly larger than the diameter of pin 71. A drilled hole of approximately the same diameter as that of deflated balloon 82 is provided in the bone by the health care technician. Balloon implant 68, in the deflated state, is then inserted into the hole in the bone.

Balloon implant 68 is inflated through partially hollow pin 71, which is in communication with the interior of inflatable balloon 82 by conduits 83. Any of the methods previously discussed can be utilized to inflate inflatable balloon 82. Upon inflation, inflatable balloon 82 expands in diameter to the degree desired, up to its maximum diameter, to secure the balloon implant 68 within the bone.

Figure 9A:
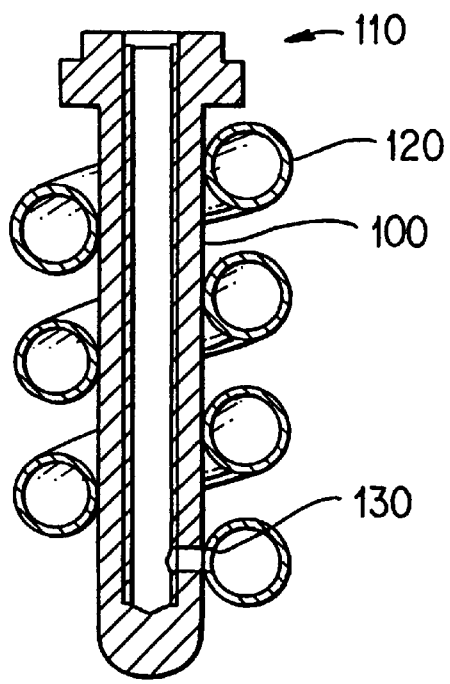
FIG. 9(a) is a cross sectional view of a further embodiment of the inflatable balloon of the present invention.
Figure 9B:
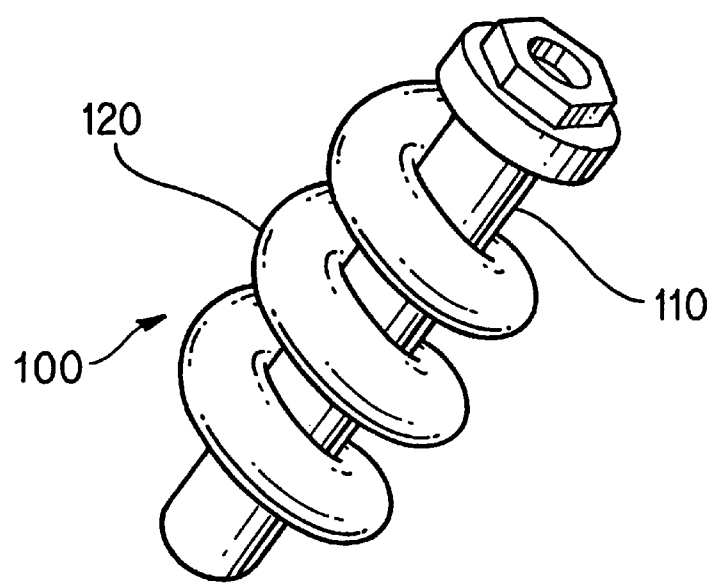
FIG. 9(b) is an isometric view of the inflatable balloon of FIG. 9(a).

A further embodiment of the invention is provided in FIGS. 9(a)–9(b). As shown therein, balloon implant 100 includes a spiral tube 120, which is wrapped around a central, basically hollow pin 110. As with the embodiment of FIG. 8, it is preferred that the tube 120 be welded to pin 110, although other suitably secure attachment methods can be used as well. In the balloon implant's deflated state, the spiral tube 120 is compressed or folded against the central pin 110 (e.g. by folding or flattening the balloon), to provide a small insertion profile for the implant. Upon insertion of the small insertion profile implant into the bone, the balloon implant can be inflated via the central pin 110 and connecting conduit 130 to expand the spiral tube 120 to the degree desired, up to the balloon implant's maximum diameter. As with the embodiment of FIG. 8, any of the methods previously described can be used to inflate the balloon implant 100.

Upon inflation of the balloon implants of the present invention, a tooth abutment and a tooth can be attached to the implant to receive functional loading. The tooth abutment can be attached to the implant by using a screw which threads into pin 71 or 110 and which holds the tooth abutment thereon.

Having described this invention with regard to specific embodiments, it is to be understood that the description is not meant as a limitation since further modifications and variations may be apparent or may suggest themselves to those skilled in the art. It is intended that the present application cover all such modifications and variations as fall within the scope of the appended claims.

I claim:

1. A dental assembly, comprising:
    a dental implant, said dental implant comprising an inflatable metal or metal alloy balloon having a hollow interior, said inflatable balloon having a first relative, smaller diameter, said implant being provided with an insertion end for insertion into a pre-formed bore in a patient's jawbone and an attachment end for attachment of a dental prosthesis, said inflatable balloon having an opening into said hollow interior, said inflatable balloon comprising walls, said walls being expandable outwardly to form a second, relatively larger diameter upon inflation of said dental implant by filling of said hollow interior with a filler material.

2. A dental assembly as claimed in claim 1, wherein said walls comprise stainless steel.

3. A dental assembly as claimed in claim 1, wherein said walls are comprised of material selected from the group of titanium, tantalum, and platinum.

4. A dental assembly as claimed in claim 1, wherein said walls comprise shape memory metal.

5. A dental assembly as claimed in claim 4, wherein said walls comprise Nitinol.

6. A dental assembly as claimed in claim 1, wherein said walls comprise a biocompatable material.

7. A dental assembly as claimed in claim 1, wherein said filler material comprises a solidifying cement.

8. A dental assembly as claimed in claim 7, wherein said solidifying cement comprises MIRACLE MIX.

9. A dental assembly as claimed in claim 1, wherein said filler material comprises bone cement.

10. A dental assembly as claimed in claim 1, wherein said filler material comprises an incompressible fluid.

11. A dental assembly as claimed in claim 1, further comprising a valve for insertion of said filler material into said dental implant.

12. A dental assembly as claimed in claim 1, wherein said filler material can be caused to change its phase from fluid to solid using a source external to said implant.

13. A dental assembly as claimed in claim 12, wherein said source comprises a heat source.

14. A dental assembly as claimed in claim 1 further comprising a partially hollow inflator pin in fluid communication with said walls.

15. A dental assembly as claimed in claim 14 wherein said attachment end comprises an inflator pin having a connecting conduit between the interior of said inflator pin and said hollow interior.

16. A dental assembly as claimed in claim 15 wherein said inflatable balloon comprises a spiral tube wrapped around said inflator pin.

\* \* \* \* \*